(12) United States Patent
Toriyabe et al.

(10) Patent No.: US 8,729,116 B2
(45) Date of Patent: May 20, 2014

(54) TRIAZOLE COMPOUND HAVING PESTICIDAL ACTIVITIES

(75) Inventors: Keiji Toriyabe, Iwata (JP); Jun Inoue, Taitoh-ku (JP); Masaaki Komatsu, Taitoh-ku (JP)

(73) Assignees: Kumiai Chemical Industry Co., Ltd., Tokyo (JP); Ihara Chemical Industry Co., Ltd., Tokyo (JP)

( * ) Notice: Subject to any disclaimer, the term of this patent is extended or adjusted under 35 U.S.C. 154(b) by 2 days.

(21) Appl. No.: 13/642,972

(22) PCT Filed: May 27, 2011

(86) PCT No.: PCT/JP2011/062262
§ 371 (c)(1),
(2), (4) Date: Oct. 23, 2012

(87) PCT Pub. No.: WO2011/152320
PCT Pub. Date: Dec. 8, 2011

(65) Prior Publication Data
US 2013/0046002 A1 Feb. 21, 2013

(30) Foreign Application Priority Data
Jun. 1, 2010 (JP) ................................. 2010-125451

(51) Int. Cl.
*A61K 31/4196* (2006.01)
*C07D 249/08* (2006.01)

(52) U.S. Cl.
USPC ........................................ 514/383; 548/265.6

(58) Field of Classification Search
USPC ........................................ 514/383; 548/265.6
See application file for complete search history.

(56) References Cited

U.S. PATENT DOCUMENTS

2009/0076282 A1 3/2009 Toriyabe et al.

FOREIGN PATENT DOCUMENTS

JP 2007 284356 11/2007
WO 2006 043635 4/2006

OTHER PUBLICATIONS

Fogassy, Ememér. Optical resolution methods. The Royal Society of Chemistry. Organic & Biomolecular Chemistry. (4), (2006), 3011-3030.*
Miyazaki, A., "Studies on the Absolute Stereochemistry in Metabolism and Activity Development of Insecticides," Journal of Pesticide Science, vol. 19, pp. S107 to S114, (1994).
Gadepalli, R. S., et al., "Synthesis of Fenthion Sulfoxide and Fenoxon Sulfoxide Enantiomers: Effect of Sulfur Chirality on Acetylcholinesterase Activity," Chemical Research in Toxicology, vol. 20, No. 2, pp. 257 to 262, (2007).
Buronfosse, T., et al., Stereoselective Sulfoxidation of the Pesticide Methiocarb by Flavin-Containing Monooxygenase and Cytochrome P450-Dependent Monooxygenases of Rat Liver Microsomes. Anticholinesterase Activity of the Two Sulfoxide Enantiomers, Journal of Biochemical Toxicology, vol. 10, No. 4, pp. 179 to 189, (1995).
International Search Report Issued Aug. 16, 2011 in PCT/JP11/062262 Filed May 27, 2011.

* cited by examiner

*Primary Examiner* — Samantha Shterengarts
(74) *Attorney, Agent, or Firm* — Oblon, Spivak, McClelland, Maier & Neustadt, L.L.P.

(57) ABSTRACT

To provide a triazole compound which has remarkably excellent pesticidal activities. Optically active (+)-1-[2-fluoro-4-methyl-5-(2,2,2-trifluoroethylsulfinyl)phenyl]-5-amino-3-(trifluoromethyl)-1H-1,2,4-triazole represented by the following formula (I), which is obtainable by subjecting a racemic modification of 1-[2-fluoro-4-methyl-5-(2,2,2-trifluoroethylsulfinyl)phenyl]-5-amino-3-(trifluoromethyl)-1H-1,2,4-triazole to optical resolution:

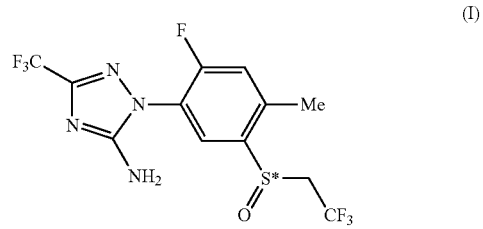

(I)

6 Claims, No Drawings

TRIAZOLE COMPOUND HAVING PESTICIDAL ACTIVITIES

TECHNICAL FIELD

The present invention relates to optically active (+)-1-[2-fluoro-4-methyl-5-(2,2,2-trifluoroethylsulfinyl)phenyl]-5-amino-3-(trifluoromethyl)-1H-1,2,4-triazole and a pesticide comprising it as an active ingredient.

BACKGROUND ART

Pesticides to be used against pests are usually desired to be chemicals which exhibit sufficient controlling effects against a wide range of pests at low doses and further are capable of maintaining such effects for a certain period of time, when applied to pests, useful plants or useful crop plants, or to soil for vegetation of useful plants or useful crop plants or in the vicinity thereof. Especially, in recent years, from the environmental problems, it has been desired to develop a pesticide which is safer and has excellent pesticidal activities at a low dose.

On the other hand, Patent Document 1, discloses 1-[2-fluoro-4-methyl-5-(2,2,2-trifluoroethylsulfinyl)phenyl]-5-amino-3-(trifluoromethyl)-1H-1,2,4-triazole, and it is disclosed that such a compound is useful as a pesticide. The compound has an asymmetric sulfur atom, and therefore, presence of optical isomers is expected, however, Patent Document 1, discloses nothing about optical isomers.

PRIOR ART DOCUMENT

Patent Document

Patent Document 1:, WO2006/43635

DISCLOSURE OF INVENTION

Technical Problem

The present invention has been made under such circumstances, and it is to provide optically active (+)-1-[2-fluoro-4-methyl-5-(2,2,2-trifluoroethylsulfinyl)phenyl]-5-amino-3-(trifluoromethyl)-1H-1,2,4-triazole which has excellent pesticidal activities at a low dose.

Solution to Problem

As a result of an extensive study, the present inventors have found that (+)-1-[2-fluoro-4-methyl-5-(2,2,2-trifluoroethylsulfinyl)phenyl]-5-amino-3-(trifluoromethyl)-1H-1,2,4-triazole being a specific optical isomer (enantiomer) in the compound disclosed in the above-mentioned Patent Document 1,, unexpectedly exhibits pesticidal activities far superior to another corresponding optical isomer (enantiomer) or to the corresponding racemic modification.

The present invention is based on such a discovery and provides the following.

(1) Optically active (+)-1-[2-fluoro-4-methyl-5-(2,2,2-trifluoroethylsulfinyl)phenyl]-5-amino-3-(trifluoromethyl)-1H-1,2,4-triazole represented by the formula (I):

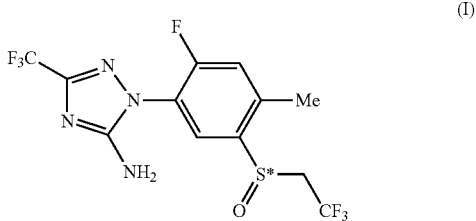

(I)

(2) A pesticide for controlling a pest, which comprises, as an active ingredient, the optically active (+)-1-[2-fluoro-4-methyl-5-(2,2,2-trifluoroethylsulfinyl)phenyl]-5-amino-3-(trifluoromethyl)-1H-1,2,4-triazole as defined in the above (1).

(3) The pesticide according to the above (2), wherein the pest is pest orthoptera, pest thysanoptera, pest hemiptera, pest coleoptera, pest diptera, pest lepidoptera, pest hymenoptera, pest collembola, pest thysanura, pest blattaria, pest isoptera, pest psocoptera, pest mallophaga, pest anoplura, a plant-parasitic mite, a plant-parasitic nematode, a plant-parasitic mollusc, an unfavorable animal, an insanitary insect, or a parasite.

(4) The pesticide according to the above (2), wherein the pest is a plant-parasitic mite, a plant-parasitic nematode, or pest diptera.

(5) A method for controlling a pest, which comprises applying the optically active (+)-1-[2-fluoro-4-methyl-5-(2,2,2-trifluoroethylsulfinyl)phenyl]-5-amino-3-(trifluoromethyl)-1H-1,2,4-triazole as defined in the above (1).

(6) A method for producing optically active (+)-1-[2-fluoro-4-methyl-5-(2,2,2-trifluoroethylsulfinyl)phenyl]-5-amino-3-(trifluoromethyl)-1H-1,2,4-triazole, which comprises subjecting a racemic modification of 1-[2-fluoro-4-methyl-5-(2,2,2-trifluoroethylsulfinyl)phenyl]-5-amino-3-(trifluoromethyl)-1H-1,2,4-triazole to optical resolution.

Advantageous Effects of Invention

The optically active (+)-1-[2-fluoro-4-methyl-5-(2,2,2-trifluoroethylsulfinyl)phenyl]-5-amino-3-(trifluoromethyl)-1H-1,2,4-triazole of the present invention exhibits remarkably excellent pesticidal activities at a low dose, as compared with its optical isomer i.e. optically active (−)-1-[2-fluoro-4-methyl-5-(2,2,2-trifluoroethylsulfinyl)phenyl]-5-amino-3-(trifluoromethyl)-1H-1,2,4-triazole or its racemic modification i.e. 1-[2-fluoro-4-methyl-5-(2,2,2-trifluoroethylsulfinyl)phenyl]-5-amino-3-(trifluoromethyl)-1, H-1,2,4-triazole, and thus is useful as a pesticide.

DESCRIPTION OF EMBODIMENTS

Now, the present invention will be described in detail.

In the present invention, "(+)-1-[2-fluoro-4-methyl-5-(2,2,2-trifluoroethylsulfinyl)phenyl]-5-amino-3-(trifluoromethyl)-1H-1,2,4-triazole" is preferably composed solely of the (+) isomer. However, depending upon the optical resolution method, the (−) isomer as its optical isomer may not be completely separated, and in such a case, it may contain the (−) isomer at a level of from 1, to 20, mol %.

The (+)-1-[2-fluoro-4-methyl-5-(2,2,2-trifluoroethylsulfinyl)phenyl]-5-amino-3-(trifluoromethyl)-1H-1,2,4-triazole of the present invention (hereinafter referred to simply as the compound of the present invention) can be produced usually by subjecting a racemic modification represented by the formula (II):

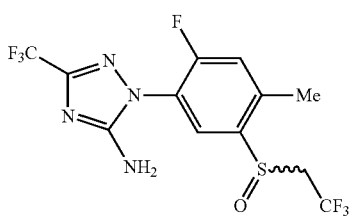

(II)

to optical resolution. As a method for such optical resolution, it is possible, for example, to resolve the racemic modification into the (+) optical isomer and the (−) optical isomer by means of a high performance liquid chromatography column for separation of optical isomers. The high performance chromatography column for separation of optical isomers is commercially available, and for example, CHIRAL PAK AD manufactured and sold by DAICEL CHEMICAL INDUSTRIES, LTD. may be used.

The solvent to be used for the optical resolution may, for example, be an aliphatic hydrocarbon such as hexane or heptane; an alcohol such as methanol, ethanol, propanol, 2-propanol or butanol; a halogenated hydrocarbon such as dichloromethane or chloroform; an ether such as diethyl ether, 1,2-dimethoxyethane, diisopropyl ether, tetrahydrofuran or dioxane; a nitrile such as acetonitrile; acetic acid; water; or a mixed solvent thereof. Among them, hexane or 2-propanol may, for example, be preferably used as the solvent.

The temperature and time for the optical resolution may be changed within wide ranges. Usually, the temperature is from −20, to 60° C., preferably from 5, to 50° C. The time is usually from 0.01, hour to 50, hours, preferably from 0.1, hour to 2, hours.

When the compound of the present invention is used as the active ingredient of a pesticide, it may be used by itself. However, it can be formulated into various formulations such as an emulsifiable concentrate, a dust, a granule, a tablet, a wettable powder, a water-soluble concentrate, a liquid formulation, a flowable, a water dispersible granule, an aerosol, a paste, an oil miscible solution and a smoking agent in combination with various carriers, surfactants and other adjuvants which are commonly used for formulation as agricultural adjuvants.

In such a case, the blend proportions of the compound of the present invention and the agricultural adjuvants are usually such that the compound of the present invention is from 0.1, to 90, mass %, preferably from 1, to 70, mass % and the agricultural adjuvants are from 10, to 99.9, mass %, preferably from 20, to 90, mass %, based on the entire amount (100, mass %) of the pesticide.

The carriers to be used for such formulation may be classified into solid carriers and liquid carriers.

The solid carriers include, for example, animal and plant powders such as starch, activated carbon, soybean powder, wheat flour, wood flour, fish flour and powdered milk, and mineral powders such as talc, kaolin, bentonite, calcium carbonate, zeolite, diatomaceous earth, white carbon, clay, alumina, ammonium sulfate and urea.

The liquid carriers include, for example, water; alcohols such as isopropyl alcohol and ethylene glycol; ketones such as cyclohexanone, methyl ethyl ketone and isophorone; ethers such as dioxane and tetrahydrofuran; aliphatic hydrocarbons such as kerosene and light oil; aromatic hydrocarbons such as xylene, trimethylbenzene, tetramethylbenzen, methylnaphthalene and solvent naphtha; halogenated hydrocarbons such as chlorobenzene; acid amides such as dimethylacetamide; esters such as glycerin esters of fatty acids; nitriles such as acetonitrile; and sulfur-containing compounds such as dimethyl sulfoxide.

The surfactants include, for example, metal salts of alkylbenzenesulfonic acids, metal salts of dinaphthylmethanedisulfonic acids, salts of alcohol sulfates, alkylarylsulfonates, lignin sulfonates, polyoxyethylene glycol ethers, polyoxyethylene alkyl aryl ethers, polyoxyethylene sorbitan monoalkylates and salts of a formalin condensate of naphthalenesulfonate.

The other adjuvants include, for example, adhesive agents and thickeners such as carboxymethylcellulose, gum arabic, sodium arginate, guar gum, tragacanth gum, and polyvinyl alcohol; antifoaming agents such as metal soap; physical property improvers such as fatty acids, alkyl phosphate salts, silicone and paraffin; and coloring agents.

When these formulations are practically used, they may be used directly or after diluted with a diluent such as water to a predetermined concentration.

Various formulations containing the compound of the present invention, whether diluted or not, may be applied by conventional methods, i.e., application methods (such as spraying, misting, atomizing, dusting, granule application, paddy water application and seeding box application), soil treatment (such as mixing or drenching), surface application (such as painting, dressing and covering), dipping, poison bait or smoking.

Further, the above active ingredient may be incorporated into livestock feeds so as to prevent infestation or growth of pests, especially pest insects after it is voided in excrement.

Otherwise, it can also be applied by a so-called ultra-low volume, high concentration application method. The proportion of the active ingredient in a pesticide in the case of the ultra-low volume, high concentration application method, is suitably selected as required, and it is from 0.1, to 20, mass %, preferably from 0.5, to 10 mass % in the case of a dust or a granule, and from 1, to 80% mass %, preferably from 10, to 50, mass % in the case of an emulsifiable concentrate or a wettable powder.

The pesticides of the present invention are applied, when they are diluted with a diluent, usually at an active ingredient concentration of from 0.1, to 5,000, ppm. When they are used directly, the dose per unit area is from 0.1, to 5,000, g, preferably from 5, to 2,000, g per 1, ha in terms of the compound that serves as the active ingredient. However, the dose is not limited to such specific range.

The compound of the present invention exhibits excellent pesticidal effects against pests such as pest orthoptera, pest thysanoptera, pest hemiptera, pest coleoptera, pest diptera, pest lepidoptera, pest hymenoptera, pest collembola, pest thysanura, pest blattaria, pest isoptera, pest psocoptera, pest mallophaga, pest anoplura, plant-parasitic mites, plant-parasitic nematodes, plant-parasitic molluscs, other pests, unfavorable animals, insanitary insects or parasites, and it has particularly excellent pesticidal activities against plant-parastic mites, plant-parastic nematodes or pest diptera.

Plant-parasitic mites may, for example, be family Eupodidae, blue oat mite (*Penthaleus major*), etc., family Tarsonemidae, cyclamen mite (*Phytonemus pallidus*), broad mite (*Polyphagotarsonemus latus*), etc., family Pyemotidae, one of pyemotesmite (*Siteroptes*, sp.), etc., family Tenuipalpidae, citrus flat mite (*Brevipalpus lewisi*), etc., family Tuckerellidae, tuckerellid mite (*Tuckerella pavoniformis*), etc., family Tetranychidae, apricot spider mite (*Eotetranychus boreus*), citrus red mite (*Panonychus citri*), European red mite (*Panonychus ulmi*), two-spotted spider mite (*Tetranychus*

*urticae*), Kanzawa spider mite (*Tetranychus kanzawai*), etc., family Phytoptidae, *Trisetacus pini*, etc., family Eriophyidae, pink citrus rust mite (*Aculops pelekassi*), tomato rust mite (*Aculops lycopersici*), tea rust mite (*Acaphylla theavagrans*), pear rust mite (*Epitrimerus pyri*), citrus rust mite (*Phyllocoptruta oleivora*), etc., family Diptilomiopidae, *Diptacus crenatae*, etc., family Acaridae, brown legged grain mite (*Aleuroglyphus ovatus*), mould mite (*Tyrophagus putrescentiae*), bulb mite (*Rhizoglyphus robini*), etc., but not limited thereto.

Plant-parasitic nematodes may, for example, be family Meloidogynidae, southern root-knot nematode (*Meloidogyne incognita*), tropical root-knot nematode (*Meloidogeyne javanica*), northern root-knot nematode (*Meloidogyne hapla*), peanut root-knot nematode (*Meloidogyne arenaria*), Columbia root-knot nematode (*Meloidogyne chitwoodi*), Thames' root-knot nematode (*Meloidogyne thamesi*), etc., family Anguinidae, potato rot nematode (*Ditylenchus destructor*), stem nematode (*Ditylenchus dipsaci*), rice stem nematode (*Ditylenchus angustus*), etc., family Pratylenchidae, northern root lesion nematode (*Pratylenchus penetrans*), lesion nematode (*Pratylenchus fallax*), root lesion nematode (*Pratylenchus coffeae*), Walnut meadow nematode (*Pratylenchus vulnus*), banana root nematode (*Radopholus similis*), citrus burrowing nematode (*Radopholus citrophilus*), false root-knot nematode (*Nacobbus aberrans*), etc., family Heteroderidae, potato cyst nematode (*Globodera rostochiensis*), White potato cyst-nematode (*Globodera pallida*), soybean cyst nematode (*Heterodera glycines*), sugarbeet nematode (*Heterodera shachtoii*), etc., family Aphlenchidae, mycophagous nematode worm (*Aphelenchus avenae*), etc., family Parasitaphelenchidae, pine wood nematode (*Bursaphelenchus xylophilus*), etc., family Longidoridae, California dagger nematode (*Xiphinema index*), etc., family Paratylenchidae, (*Paratylenchus curvitatus*), etc., family Aphelenchoididae, rice white tip nematode (*Aphelenchoides besseyi*), etc., but not limited thereto.

Pest diptera may, for example, be family Tipulidae, rice crane fly (*Tipula aino*), etc., family Chironomidae, *Tanytarsus oryzae*, (*Tanytarsus oryzae*), family Cecidomyiidae, rice gall midge (*Orseolia oryzae*), hessian fly (*Mayetiola destructor*), etc., family Tephritidae, Mediterranean fruit fly (*Ceratitis capitata*), melon fly (*Bactrocera cucurbitae*), guava fruit fly (*Bactrocera correcta*), oriental fruit fly (*Bactrocera dorsalis*), Ethiopian fruit fly (*Dacus ciliatus*), Baluchistan melon fly (*Myiopardalis pardalina*), Fruit fly (*Monacrostichus citricola*), cherry fruit fly (*Rhagoletis cerasi*), cherry fruit fly (*Rhaholetis cingulata*), (*Chaetostomella stigmata*), Japanese cherry fruit fly (*Euphranta japonica*), (*Trupanea amoena*), etc., family Ephydridae, rice leafminer (*Hydrellia griseola*), rice whorl maggot (*Hydrellia sasakii*) etc., family Drosophilidae, cherry *drosophila*, (*Drosophila suzukii*), Fruit fly (*Drosophila simulans*), etc., frit-fly (*Oscinella frit*), rice stem maggot (*Chlorops oryzae*), family Agromyzidae, (*Ophiomyia phaseoli*), American serpentine leafminer (*Liriomyza trifolii*), vegetable leafminer (*Liriomyza sativae*), tomato leaf miner (*Liriomyza bryoniae*), garden pea leafminer (*Chromatomyia horticola*), leaf miner (*Liriomyza huidobrensis*), etc., family Anthomyiidae, spinach leafminer (*Pegomya hyoscyami*), cabbage fly (*Delia radicum*), seed-corn fly (*Hylemia platura*), etc., family Muscidae, (*Atherigona soccata*), housefly (*Musca domestica*), stable fly (*Stomoxys calcitrans*), etc., family Gastrophilidae, horse bot fly (*Gasterophilus intestinalis*), etc., family Culicidae, yellow fever mosquito (*Aedes aegypti*), common house mosquito (*Culex pipiens*), malaria vector (*Anopheles slnensis*), vector of Japanese encephalitis (*Culex tritaeniorhynchus*), etc., but not limited thereto.

The compound of the present invention exhibits pesticidal effects also against the above-described pests which have acquired resistance to existing pesticides, etc.

The compound of the present invention is useful for useful plants and useful crop plants. The useful plants and useful crop plants include, for example, agricultural crops such as corn, rice, wheat, barley, rye, oat, sorghum, cotton, soybean, peanut, buckwheat, sugar beet, rapeseed, sunflower, sugar cane and tobacco; vegetables such as solanaceous vegetables (such as eggplants, tomatoes, green pepper, hot pepper, potatoes, etc.), cucurbitaceous vegetables (such as cucumbers, pumpkins, zucchini, watermelon, melon, etc.), cruciferous vegetables (such as radish, turnip, horseradish, kohlrabi, Chinese cabbage, cabbage, Chinese mustard, broccoli, cauliflower, etc.), asteraceous vegetables (such as burdock, crown daisy, Artichoke, lettuce, etc.), family Liliaceae vegetables (such as green onion, onion, allium and asparagus), umbelliferous vegetables (such as carrot, parsley, celery, parsnip, etc.), chenopodiaceous vegetables (such asspinach, chard, etc.), mint family vegetables (such as Japanese basil, mint, basil, etc.), strawberry, sweet potato, Japanese yam, and *Colocasia esculenta*; fruits such as pome fleshy fruits (such as apples, pear, Japanese pear, Chinese quince, quince, etc.), stone fleshy fruits (such as peach, *Prunus salicina*, nectarine, *Prunus mume, Prunus avium*, apricot, prune, etc.), citrus (such as citrus unshiu, orange, lemon, lime, grapefruit, etc.), nuts (such as chestnut, walnut, hazel, almond, pistachio, cashew nut, macadamia nut, etc.), berries (such as blueberry, cranberry, blackberry, raspberry, etc.), grapes, Japanese persimmon, olive, loquat, banana, coffee, date palm, coconut palm, and Elaeis guineensis; trees other than fruit trees, such as tea, mulberry tree, roadside trees (such as Japanese ash, birch, dogwood, eucalyptus, ginkgo tree, lilac, maple, oak, poplar, cercis, liquidambar, plane tree, zelkova, Japanese arborvitae, fir tree, hemlock fir, juniper, pine, spruce, yew, elm tree, horse chesnut, etc.), *Viburnum odoratissimum, Podocarpus macrophyllus, Cryptomeria japonica*, Japanese cypress, croton, *Euonymus japonicas*, and *Photinia glabra*; grasses such as Zoysia (such as wild lawn grass, Korean lawn grass, etc.), bermudagrasses (such as *Cynodon dactylon*), bent grass (such as herd's-grass, creeping bent grass, *Agrostis capillaris*, etc.), bluegrasses (such as Kentucky bluegrass, rough bluegrass, etc.), *Festuca* (such as *Festuca arundinacea, Festuca rubra*, var. commutate, *Festuca rubra* L. var. genuina Hack, etc.), ryegrasses (such as darnel, rye grass, etc.), orchard grass, and timothy grass; oilseed crops such as oil palm and *Jatropha curcas*; flowers and ornamental plants (such as roses, carnation, *Chrysanthemum morifolium, Eustoma grandiflorum*, gypsophila, gerbera daisy, marigold, salvia, petunia, verbena, tulips, aster, gentian, lily, pansy, cyclamen, orchid, lily of the valley, lavender, stock, ornamental cabbage, *Primula*, poinsettia, gladiolus, cattleya, daisy, verbena, *Cymbidium*, begonia, etc.); foliage plants; etc., but not limited thereto.

The compound of the present invention can be used for plants which have acquired characteristics such as resistance to pests, resistance to diseases or resistance to herbicides, by gene recombination, artificial hybridization, etc. Further, it has controlling effects also against pests which show resistance to existing pesticides, miticides or nematicides, such as organophosphorus compounds, carbamate compounds, synthetic pyrethroid compounds, acylurea compounds or conventional insecticides.

The compound of the present invention is, of course, sufficiently effective when used alone. However, it may be used, if necessary, in combination or in admixture with fertilizers or other agrochemicals such as insecticides, miticides, nematicides, fungicides, antivirus agents, attractants, herbicides and plant growth modulating agents, and such combined or admixed use can sometimes produce improved effects.

In a case where the compound of the present invention and at least one member selected from other pesticidally active components are to be applied in combination, they are applied usually in a mass ratio of 100:0 to 1:100, preferably from 20:1 to 1:20.

When it is used in combination with other pesticidally active components or fertilizers, the respective formulations of individual components may be mixed for use at the time of the application. Otherwise, the respective formulations of the individual components may successively be used, or may be applied at intervals. When they are applied at intervals, they may be applied at intervals of from about one day to 40 days, although the intervals may vary depending upon other components to be used.

Now, among other pesticidally active components which may be mixed or used in combination with the compound of the present invention, known insecticides, miticides, nematicides and synergists will be exemplified, but such other components are not limited to the exemplified ones.

[Insecticides, Miticides and Nematicides]

1. Acetylcholinesterase Inhibitors:

Carbamate compounds: alanycarb, aldicarb, aldoxycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, 3,5-xylyl methylcarbamate (XMC) and xylylcarb.

(1B) Organic Phosphorus Compounds:

acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diamidafos, diazinon, dichlorvos, dicrotophos, dimethoate, dimethylvinphos, dioxabenzofos, disulfoton, DSP, EPN, ethion, ethoprophos, etrimfos, famphur, fenamiphos, fenitrothion, fenthion, fonofos, fosthiazate, fosthietan, heptenophos, isamidofos, isazophos, isofenphos-methyl, isopropyl O-methoxyaminothio-phosphoryl salicylate, isoxathion, malathion, mecarbam, methamidophos, methidathion, mevinphos, monocrotophos, naled, omethoate, oxydemeton-methyl, oxydeprofos, parathion, parathion-methyl, phenthoate, phorate, phosalone, phosmet, phosphamidon, phoxim, pirimiphos-methyl, profenofos, propaphos, propetamphos, prothiofos, pyraclofos, pyridaphenthion, quinalphos, sulfotep, tebupirimfos, temephos, terbufos, tetrachlorvinphos, thiometon, thionazin, triazophos, trichlorfon, vamidothion, dichlofenthion, imicyafos, isocarbophos, mesulfenfos and flupyrazofos.

2. GABA Receptor (Chloride Channel) Inhibitors (2A) Cyclodiene Organic Chlorinated Compounds: chlordane, endosulfan and gamma-BCH.

(2B) Phenylpyrazole Compounds: acetoprol, ethiprole, fipronil, pyrafluprole, pyriprole and RZI-02-003, (Code Number).

3. Agents Acting on Sodium Channel (3A) Pyrethroid Compounds: acrinathrin, allethrin [including d-cis-trans and d-trans], bifenthrin, bioallethrin, bioallethrin S-cyclopentenyl, bioresmethrin, cycloprothrin, cyfluthrin [including beta-], cyhalothrin [including gamma- and lambda-], cypermethrin [including alpha-, beta-, theta- and zeta-], cyphenothrin [including (1R)-trans-isomers], deltamethrin, empenthrin, esfenvalerate, etofenprox, fenpropathrin, fenvalerate, flucythrinate, flumethrin, tau-fluvalinate [including tau-], halfenprox, imiprothrin, metofluthrin, permethrin, phenothrin [including (1R)-trans-isomer], prallethrin, profluthrin, pyrethrine, resmethrin, RU15525, (code number), silafluofen, tefluthrin, tetramethrin, tralomethrin, transfluthrin, ZXI8901, (code number), fluvalinate, tetramethylfluthrin and meperfluthrin.

(3B) DDT Compounds: DDT, and methoxychlor.

4. Nicotinic Acetylcholine Receptor Agonist/Antagonist (4A) Neo Nicotinoid Compounds: acetamiprid, clothianidin, dinotefuran, imidacloprid, nitenpyram, thiacloprid, and thiamethoxam.

(4B) Nicotine Compounds: nicotine-sulfate

5. Nicotinic Acetylcholine Receptor Allosteric Activator

Spinosyn Compounds: spinetoram and spinosad

6. Agents to Activate Chloride Channel

Abamectin/milbemycin compounds: abamectin, emamectin benzoate, lepimectin, milbemectin, ivermectin and polynactins.

7. Juvenile Hormone-Type Agents

Diofenolan, hydroprene, kinoprene, methothrin, fenoxycarb and pyriproxyfen.

8. Non-Specific Action (Many Active Sites) Agents 1,3-Dichloropropene, DCIP, ethylene dibromide, methyl bromide, chloropicrin and sulfuryl fluoride.

9. Antifeedants

Pymetrozine, flonicamid and pyrifluquinazon.

10. Growth Control Agents for Mites clofentezine, diflovidazin, hexythiazox and etoxazole.

11. Agents to Destroy Lining of Intestine of Insects.

BT agents: *Bacillus sphaericus*, *Bacillus thuringiensis* subsp. aizawai, *Bacillus thuringiensis* subsp. israelensis, *Bacillus thuringiensis* subsp. kurstaki, *Bacillus thuringiensis* subsp. tenebrionis, Bt crop proteins(Cry1Ab, Cry1Ac, Cry1Fa, Cry2Ab, mCry3A, Cry3Ab, Cry3Bb, Cry34/35Ab1), *Bacillus popilliae*, and *Bacillus subtillis*.

12. ATP Biosynthetic Enzyme Inhibitors

Diafenthiuron;

organic tin compounds: azocyclotin, cyhexatin and fenbutatin oxide;

propargite and tetradifon.

13. Uncouplers

Chlorfenapyr and DNOC.

14. Nicotinic Acetylcholine Channel Blockers

Nereis-toxin Compounds: bensultap, cartap, thiocyclam and thiosultap.

15. Chitin Biosynthesis Inhibitors (type 0)

Benzoylurea compounds: bistrifluron, chlorfluazuron, diflubenzuron, flucycloxuron, flufenoxuron, hexaflumuron, lufenuron, novaluron, noviflumuron, teflubenzuron, triflumuron and fluazuron.

16. Chitin Biosynthesis Inhibitors (type 1)

Buprofezin

17. Molting Inhibitor (Against Diptera)

Cyromazine

18. Ecdysone Agonist (Molt-Accelerating)

Diacylhydrazine Compounds: chromafenozide, halofenozide, methoxyfenozide and tebufenozide.

19. Octopaminergic Agonist

Amitraz

20. Mitochondrial Electron Transport System (Composite III) Inhibitors cyflumetofen, hydramethylnon, acequinocyl, fluacrypyrim and cyenopyrafen.

21. Mitochondrial Electron Transport System (Composite I) Inhibitors

METI mitecides: fenazaquin, fenpyroximate, pyridaben, pyrimidifen, tebufenpyrad and tolfenpyrad.

Other: rotenone

22. Sodium Channel Inhibitors
   Indoxacarb and metaflumizon.
23. Lipogenesis Inhibitors
   Tetranic insecticides/miticides: spirodiclofen, spiromesifen and spirotetramat.
24. Mitochondrial Electron Transport System (Composite IV) Inhibitors
   Aluminium phosphide, phosphine, zinc phosphide and calcium cyanide.
25. Neural Inhibitor (Mechanism of Action Unknown)
   Bifenazate
26. Aconitase Inhibitor
   Sodium fluoroacetate
27. Agents Acting on Ryanodine Receptor
   Chlorantraniliprole, flubendiamide and cyantraniliprole
28. Other Agents (Activities Unknown)
   Azadirachtin, amidoflumet, benclothiaz, benzoximate, bromopropylate, chinomethionat, CL900167 (code number), cryolite, dicofol, dicyclanil, dienochlor, dinobuton, fenbutatin oxide, fenothiocarb, fluensulfone, flufenerim, flusulfamide, karanjin, metham, methoprene, methoxyfenozide, methyl isothiocyanate, pyridalyl, pyrifluquinazon, sulcofuron-sodium, sulflramid and sulfoxaflor.
29. Synergists
   piperonyl butoxide and DEF.

EXAMPLES

Now, the method for producing the compound of the present invention, the formulation method and the use will be described in detail with reference to Examples, but it should be understood that the present invention is by no means thereby restricted.

The compound of the present invention i.e. optically active (+)-1-[2-fluoro-4-methyl-5-(2,2,2-trifluoroethylsulfinyl) phenyl]-5-amino-3-(trifluoromethyl)-1H-1,2,4-triazole can be produced by the method shown by the following Examples.

Production of optically active (+)-1-[2-fluoro-4-methyl-5-(2,2,2-trifluoroethylsulfinyl)phenyl]-5-amino-3-(trifluoromethyl)-1H-1,2,4-triazole (compound No. I)

653.6, mg of racemic 1-[2-fluoro-4-methyl-5-(2,2,2-trifluoroethylsulfinyl)phenyl]-5-amino-3-(trifluoromethyl)-1H-1,2,4-triazole (compound No. II) was dissolved in 2-propanol (100 mL), and n-hexane (100 mL) was added to prepare a sample solution.

The above sample solution was treated by high performance liquid chromatography under conditions of a flow rate of 7.0 mL/min at room temperature by using CHIRAL PAK AD, manufactured and sold by DAICEL CHEMICAL INDUSTRIES, LTD. (inner diameter 2 cm×length 25 cm) and using as a mobile phase a solvent mixture of n-hexane/2-propanol=60/40 (volume ratio), and analyzed by an ultraviolet absorption detector (250 nm), whereby a peak (peak 1) at a retention time of 10 minutes and a peak (peak 2) at a retention time of 20 minutes were obtained.

The respective peak components were repeatedly separated, and the separated solutions were vacuum-concentrated at 60° C. to obtain crystals corresponding to peaks 1 and 2 in amounts of 266.7 mg and 256.2 mg, respectively. The respective optical resolutions were measured, whereby the component of peak 1 showed a specific optical rotation $[\alpha]_D^{25}=-77.8°$ (C=0.20/methanol), and the component of peak 2 showed a specific optical rotation $[\alpha]_D^{25}=+77.8°$ (C=0.20/methanol)

The above component of peak 2 is the desired (+)-1-[2-fluoro-4-methyl-5-(2,2,2-trifluoroethylsulfinyl)phenyl]-5-amino-3-(trifluoromethyl)-1H-1,2,4-triazole (compound No. I), and the above component of peak 1, is (−)-1-[2-fluoro-4-methyl-5-(2,2,2-trifluoroethylsulfinyl)phenyl]-5-amino-3-(trifluoromethyl)-1H-1,2,4-triazole (compound No. III).

$^1$H-NMR data of compound No. I (CDCl$_3$/TMS δ (ppm) value):
2.47(3H,s), 3.39-3.59(2H,m), 4.91(2H,bs)7.25(1H,d, J=10.2Hz), 8.17(1H,d,J=7.4 Hz)

$^1$H-NMR data of compound No. III (CDCl$_3$/TMS δ (ppm) value):
2.47(3H,s), 3.37-3.59(2H,m), 4.97(2H,bs)7.24(1H,d,J=10.2, Hz), 8.17(1H,d,J=7.4 Hz)

Here, the above $^1$H-NMR (nuclear magnetic resonance) data of the respective compounds were measured by JEOL JNM-LA400 (FT NMR SYSTEM). CDCl$_3$ means deuterated chloroform, and TMS as the reference substance means tetramethylsilane.

(Method for Producing Racemic Modification)

The racemic modification (II) can be produced by the method disclosed in Patent Document 1.

Now, formulation methods will be described in detail with reference to typical Formulation Examples. The types of the compounds and adjuvants, and their blend ratios are not limited to the following, and various changes are possible within a wide range. In the following description, part(s) means part(s) by mass.

Formulation Example 1

Emulsifiable Concentrate

| | |
|---|---|
| Compound No. I | 30 parts |
| Cyclohexanone | 20 parts |
| Polyoxyethylene alkyl aryl ether | 11 parts |
| Calcium alkylbenzenesulfonate | 4 parts |
| Methyl naphthalene | 35 parts |

The above components were uniformly dissolved to obtain an emulsifiable concentrate.

Formulation Example 2

Wettable Powder

| | |
|---|---|
| Compound No. I | 10 parts |
| Sodium salt of naphthalenesulfonic acid formalin condensate | 0.5 part |
| Polyoxyethylene alkyl aryl ether | 0.5 part |
| Diatomaceous earth | 24 parts |
| Clay | 65 parts |

The above components were uniformly mixed and pulverized to obtain a wettable powder.

Formulation Example 3

Dust

| | |
|---|---|
| Compound No. I | 2 parts |
| Diatomaceous earth | 5 parts |
| Clay | 93 parts |

The above components were uniformly mixed and pulverized to obtain a dust.

Example 4

Granule

| | |
|---|---|
| Compound No. I | 5 parts |
| Sodium lauryl alcohol sulfate | 2 parts |
| Sodium lignin sulfonate | 5 parts |
| Carboxymethyl cellulose | 2 parts |
| Clay | 86 parts |

The above components were uniformly mixed and pulverized. To this mixture, water in an amount corresponding to 20, parts was added, followed by kneading, and the kneaded product was formed into granules of 14 to 32 mesh by an extrusion granulator, which were dried to obtain a granule.

Now, the effect of the pesticide comprising the compound of the present invention as an active ingredient will be described with reference to Test Examples.

Test Example 1

Miticidal Activity Against Adults of Two-Spotted Spider Mite (Susceptible Strain) (Leaf Disk Spray Test)

A plastic cup having a capacity of 60 mL was half-filled with water, and a perforated cover was put thereon. Absorbent cotton was impregnated with water through the perforations, and two sheets of filter paper were overlaid thereon. Two leaves of kidney beans (*Phaseolus vulgaris*) cutout in a circular shape with a diameter of 2, cm, were put thereon, and ten female adults of susceptible strain two-spotted spider mite (*Tetranychus urticae*) were inoculated and left to stand overnight in a constant temperature chamber at 25° C. (photoperiod conditions: light period of 16 hours/dark period of 8 hours). After removing abnormal mites and dead mites, a pesticide prepared by diluting the test compound formulated in accordance with Formulation Example 2 with a diluent such as water, as shown in Table 1, was sprayed by an automatic spraying device (2 mg/cm$^2$). Upon expiration of two days after the treatment, the number of dead mites was counted, and the mortality was calculated by the formula 1. The test was carried out twice.

$$\text{Mortality (\%)} = \frac{\text{(Number of dead mites in treated area)} - \text{(Number of dead mites in non-treated area)}}{(10 - \text{Number of dead mites in non-treated area})} \times 100 \quad (1)$$

TABLE 1

| Test compound | | Concentration (ppm) | Mortality (%) |
|---|---|---|---|
| Compound No. I | (+)-enantiomer | 3.125 | 79 |
| Compound No. II | Racemic modification | 3.125 | 8 |
| Compound No. III | (−)-enantiomer | 6.25 | 0 |

Test Example 2

Miticidal Activity Against Adults of Two-Spotted Spider Mite (Resistant Strain) (Leaf Disk Spray Test)

A plastic cup having a capacity of 60 mL was half-filled with water, and a perforated cover was put thereon. Absorbent cotton was impregnated with water through the perforations, and two sheets of filter paper were overlaid thereon. Two leaves of kidney beans (*Phaseolus vulgaris*) cutout in a circular shape with a diameter of 2 cm, were put thereon, and ten female adults of resistant strain two-spotted spider mite (*Tetranychus urticae*) were inoculated and left to stand overnight in a constant temperature chamber at 25° C. (photoperiod conditions: light period of 16 hours/dark period of 8 hours). After removing abnormal mites and dead mites, a pesticide prepared by diluting the test compound formulated in accordance with Formulation Example 2 with a diluent such as water, as shown in Table 2 was sprayed by an automatic spraying device (2 mg/cm$^2$). Upon expiration of two days after the treatment, the number of dead mites was counted, and the mortality was calculated by the formula 1. The test was carried out twice.

TABLE 2

| Test compound | | Concentration (ppm) | Mortality (%) |
|---|---|---|---|
| Compound No. I | (+)-enantiomer | 100 | 94 |
| Compound No. II | Racemic modification | 100 | 16 |
| Compound No. III | (−)-enantiomer | 100 | 0 |

Test Example 3

Miticidal Activity Against Adults of Red Mite (Resistant Strain) (Leaf Disk Spray Test)

0.5 mass % of agar was blended to water and put into a plastic cup having a capacity of 60 mL, and two cinnamon leaf disks were put thereon and ten female adults of resistant strain red mite (*Panonychus citri*) were inoculated and left to stand overnight at a constant temperature chamber at 25° C. (photoperiod conditions: light period of 16 hours/dark period of 8 hours). After removing abnormal mites and dead mites, a pesticide prepared by diluting the test compound formulated in accordance with Formulation Example 2 with a diluent such as water, as shown in Table 3, was sprayed by an automatic spraying device (2 mg/cm$^2$). Upon expiration of two days after the treatment, the number of dead mites was counted, and the mortality was calculated by the formula 1. The test was carried out twice.

TABLE 3

| Test compound | | Concentration (ppm) | Mortality (%) |
|---|---|---|---|
| Compound No. I | (+)-enantiomer | 6.25 | 93 |
| Compound No. II | Racemic modification | 6.25 | 36 |
| Compound No. III | (−)-enantiomer | 6.25 | 0 |

Test Example 4

Penetration/Transfer Activity Against Two-Spotted Spider Mite (Susceptible Strain) (Soil Irrigation Cup Test)

To soybean (*Glycine max*) planted in a plastic cup, 35 female adults of susceptible strain two-spotted spider mite (*Tetranychus urticae*) were inoculated and left to stand overnight at a constant temperature chamber at 25° C. (photoperiod conditions: light period of 16 hours/dark period of 8 hours). A test pesticide prepared by diluting the test compound formulated in accordance with Formulation Example 2 to a predetermined concentration as disclosed in Table 4, was applied by soil drench treatment (5 mL/seedling). Upon expiration of 13 days, the number of live mites was counted, and the preventive value was calculated by the formula 2. The test was carried out twice.

$$\text{Preventive value (\%)} = \left\{ 1 - \frac{\begin{array}{c}\text{(Number of mites before}\\ \text{treatment in non-treated area)}\end{array}}{\begin{array}{c}\text{(Number of mites before}\\ \text{treatment in treated area)}\end{array}} \times \right.$$

$$\left. \frac{\begin{array}{c}\text{(Number of mites on investigated}\\ \text{day in treated area)}\end{array}}{\begin{array}{c}\text{(Number of live mites on investigated}\\ \text{day in non-treated area)}\end{array}} \right\} \times 100 \quad (2)$$

TABLE 4

| Test compound | | mga.i./ seedling | Preventive value (%) |
|---|---|---|---|
| Compound No. I | (+)-enantiomer | 0.0031 | 100 |
| Compound No. II | Racemic modification | 0.0031 | 0 |
| Compound No. III | (−)-enantiomer | 0.0031 | 0 |

Industrial Applicability

The pesticide of the present invention is an agent which exhibits sufficient controlling effects against a wide range of pests at a low dose and is further capable of maintaining such effects, and thus, it is useful for controlling pests such as plant-parasitic mites, plant-parasitic nematodes, pest dipteral, etc.

The entire disclosure of Japanese Patent Application No. 2010-125451 filed on Jun. 1, 2010 including specification, claims and summary is incorporated herein by reference in its entirety.

The invention claimed is:

1. A compound, wherein the compound is (+)-1-[2-fluoro-4-methyl-5-(2,2,2trifluoroethylsulfinyl)phenyl]-5-amino-3-(trifluoromethyl)-1H-1,2,4-triazole represented by the formula (I):

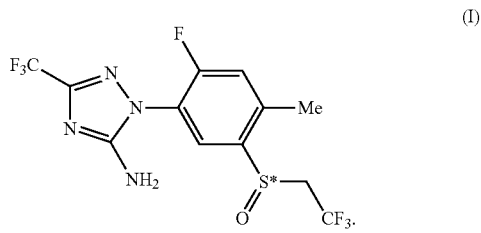

2. A pesticide for controlling a pest, which comprises, as an active ingredient, the (+)-1-[2-fluoro-4-methyl-5-(2,2,2-trifluoroethylsulfinyl)phenyl]-5-amino-3-(trifluoromethyl)-1H-1,2,4-triazole compound as defined in claim 1.

3. The pesticide according to claim 2, wherein the pest is pest orthoptera, pest thysanoptera, pest hemiptera, pest coleoptera, pest diptera, pest lepidoptera, pest hymenoptera, pest collembola, pest thysanura, pest blattaria, pest isoptera, pest psocoptera, pest mallophaga, pest anoplura, a plant-parasitic mite, a plant-parasitic nematode, a plant-parasitic mollusc, an unfavorable animal, an insanitary insect, or a parasite.

4. The pesticide according to claim 2, wherein the pest is a plant-parasitic mite, a plant-parasitic nematode, or pest diptera.

5. A method for controlling a pest, which comprises applying the (+)-1-[2-fluoro-4-methyl-5-(2,2,2-trifluoroethylsulfinyl)phenyl]-5-amino-3-(trifluoromethyl)-1H-1,2,4-triazole compound as defined in claim 1.

6. A method for producing (+)-1-[2-fluoro-4-methyl-5-(2,2,2-trifluoroethylsulfinyl)phenyl]-5-amino-3-(trifluoromethyl)-1H-1,2,4-triazole, which comprises subjecting a racemic modification of 1-[2-fluoro-4-methyl-5-(2,2,2-trifluoroethylsulfinyl)phenyl]-5-amino-3-(trifluoromethyl)-1H-1,2,4-triazole to optical resolution.

* * * * *